United States Patent [19]

Liu

[11] Patent Number: 5,260,434
[45] Date of Patent: Nov. 9, 1993

[54] DNA ENCODING IGE-BINDING PROTEIN WITH REPETITIVE SEQUENCE AND HOMOLOGY WITH IGG RECEPTOR

[75] Inventor: Fu-Tong Liu, San Diego, Calif.

[73] Assignee: The Scripps Research Institute, La Jolla, Calif.

[21] Appl. No.: 728,125

[22] Filed: Jul. 10, 1991

Related U.S. Application Data

[63] Continuation of Ser. No. 247,170, Sep. 21, 1988, abandoned, which is a continuation-in-part of Ser. No. 726,250, Apr. 23, 1985, abandoned.

[51] Int. Cl.$^5$ ............. C07H 15/12; C12P 21/06
[52] U.S. Cl. ................ 536/23.5; 435/69.1; 530/350 KC; 530/862 KC
[58] Field of Search ............. 530/387; 536/27; 435/69.1

[56] References Cited

PUBLICATIONS

Crittenden et al. *Mol. & Cell. Biol.* 4(7): 1252–1259 (1984).
Leffler et al. *Biochemistry* 28:9222–9229 (1989).
Laing et al. *J. Biol. Chem.* 264(4): 1907–1910 (1989).
Roff et al. *Biochem. J.* 211:625–629 (1983).
Cherayil et al. *J. Exp. Med.* 170:1959–1972 (1989).
Jia et al. *J. Biol. Chem.* 263(13): 6009–6011 (1988).
Martens et al. *Proc. Natl. Acad. Sci.* 82:2460–2464 (1985).
Huff et al. *J. of Immunol.* 129(2): 509–514 (1982).
Holowka et al. *Mol Immunol.* 19(2):219–227 (1982).
Albrandt et al. *Proc. Natl. Acad. Sci.* 84:6859–6863 (1987).
Liu et al. *Proc. Natl. Acad. Sci.* 82:4100–4104 (1985).

*Primary Examiner*—Robert J. Hill, Jr.
*Assistant Examiner*—Shelly J. Guest
*Attorney, Agent, or Firm*—Grant L. Hubbard

[57] ABSTRACT

An IgE-binding protein, εBP, which contains two domains: the amino-terminal domain (140 amino acids) consists of a highly conserved repetitive amino acid sequence, Tyr-Pro-Gly-Pro/Gln-Ala/Thr-Pro-Ala-Pro-Gly-Ala, whereas the carboxyl-terminal domain (122 amino acids) shares significant sequence homology with a domain of lymphocyte/macrophage receptor for the Fc portion of IgG is disclosed.

1 Claim, 10 Drawing Sheets

```
AACAGCTAGCGGAGCGGCAGGAGGAGCACTAACCAGGAAA ATG GCA GAC GGC TTC TCA CTT AAT GAT GCC TTA GCT GGC TCT      82
                                         Met Ala Asp Gly Phe Ser Leu Asn Asp Ala Leu Ala Gly Ser
                                                                       10

GGA AAC CCA AAC CCT CGA GGA TGG CCT GGT GCA GGG AAC CAG CCT GGG GCA GGA GGC TAC CCA GGG GCC TCC     157
Gly Asn Pro Asn Pro Arg Gly Trp Pro Gly Ala Gly Asn Gln Pro Gly Ala Gly Gly Tyr Pro Gly Ala Ser
                  20                                       30

TAT CCT GGG GCC TAC CCA GGA CAG GCT CCT CCA GGG GGT TAT CCT GGA CAG GCT CCT CCT AGT GCC TAT CCG GGC    232
Tyr Pro Gly Ala Tyr Pro Gly Gln Ala Pro Pro Gly Gly Tyr Pro Gly Gln Ala Pro Pro Ser Ala Tyr Pro Gly
40                                       50                                       60

CCA ACT GGC CCT AGT GCT TAT CCT GGA GCT CCA ACT GCC CCA GGG CCA ACT GCC CCC GGA GCC TTC                307
Pro Thr Gly Pro Ser Ala Tyr Pro Gly Ala Pro Thr Ala Pro Gly Pro Thr Ala Pro Gly Ala Phe
            70                                       80

CCA GGG CAA CCT GGG GGA CCT GGG GGT GGC TAC CCC AGT GCT CCC TAC CCC AGT GCT CCC TAT CCT GGG GCC TAT CCT    382
Pro Gly Gln Pro Gly Gly Pro Gly Gly Gly Tyr Pro Ser Ala Pro Tyr Pro Ser Ala Pro Tyr Pro Gly Ala Tyr Pro
90                                       100                                       110

GCT ACT GGC CCC TTT GGT GCC CCG ACT GGA CCA CTG ACA GTG CCC TAC GAT ATG CCC TTG CCT GGA GGA GTC ATG    457
Ala Thr Gly Pro Phe Gly Ala Pro Thr Gly Pro Leu Thr Val Pro Tyr Asp Met Pro Leu Pro Gly Gly Val Met
            120                                       130
```

FIG.1A

```
CCT CGC ATG CTG ATC ACA ATC ATA GGC ACA GTG AAG CCC AAC GCA AAC AGT ATC ACT CTG AAT TTC AAG AAA GGG      532
Pro Arg Met Leu Ile Thr Ile Ile Gly Thr Val Lys Pro Asn Ala Asn Ser Ile Thr Leu Asn Phe Lys Lys Gly
140                                 150                                 160

AAC GAC ATC GCC TTC CAC TTT AAC CCC CGC TTC AAT GAG AAC AAC AGA GTC ATC GTG TGC AAC ACG AAG CAG          607
Asn Asp Ile Ala Phe His Phe Asn Pro Arg Phe Asn Glu Asn Asn Arg Val Ile Val Cys Asn Thr Lys Gln
                170                                 180

GAC AAT AAC TGG GGA AGG GAA AGA CAG TCA GCT TTC CCC TTT GAG AGC GGC AAA CCA TTC AAA ATA CAG GTC          682
Asp Asn Asn Trp Gly Arg Glu Arg Gln Ser Ala Phe Pro Phe Glu Ser Gly Lys Pro Phe Lys Ile Gln Val
190                                 200                                 210

CTG GTT GAA GCC GAC CAC TTC AAG GTT GCG GTC AAT GAT GTT CAT CTG TTG CAG TAT AAC CAT CGG ATG AAG AAC      757
Leu Val Glu Ala Asp His Phe Lys Val Ala Val Asn Asp Val His Leu Leu Gln Tyr Asn His Arg Met Lys Asn
                220                                 230

CTC AGG GAA ATC AGC CAA CTG GGG ATC ATT GGT GAC ATA ACC CTC ACC AGC GCT TCC CAC GCC ATG ATC TAAGCCA     833
Leu Arg Glu Ile Ser Gln Leu Gly Ile Ile Gly Asp Ile Thr Leu Thr Ser Ala Ser His Ala Met Ile
240                                 250                                 260

GAAGGGGTGGGCCGGCACCAGAACTGCCCTGTGTGTTATGAGCGGGAAACTTTGCATTTCTCTCTCCTTATACTTCTTGTAAGACATCCATTTAATAAA    932

GTCTCGTGCTGAGAGA₉
```

| 35 | Tyr | Pro | Gly | Ala | Ser | Tyr | | Pro | Gly | Ala | 43 |
|---|---|---|---|---|---|---|---|---|---|---|---|
| 44 | Tyr | Pro | Gly | Gln | Ala | Pro | | Pro | Gly | Gly | 52 |
| 53 | Tyr | Pro | Gly | Gln | Ala | Pro | | Pro | Ser | Ala | 61 |
| 62 | Tyr | Pro | Gly | Pro | Thr | Gly | | Pro | Ser | Ala | 70 |
| 71 | Tyr | Pro | Gly | Pro | Thr | Ala | | Pro | Gly | Ala | 79 |
| 80 | Tyr | Pro | Gly | Pro | Thr | Ala | | Pro | Gly | Ala | 88 |
| 89 | Phe | Pro | Gly | Gln | Pro | Gly Gly | | Pro | Gly | Ala | 98 |
| 99 | Tyr | Pro | Ser | --- | Ala | --- | | Pro | Gly | Ala | 105 |
| 106 | Tyr | Pro | Ser | --- | Ala | --- | | Pro | Gly | Ala | 112 |
| 113 | Tyr | Pro | Ala | Thr | Gly | Pro | | Phe | Gly | Ala | 121 |

FIG.8A

| 143 | TAC | CCA | GGG | GCC | TCC | TAT | CCT | GGG | GCC | 169 |
|---|---|---|---|---|---|---|---|---|---|---|
| 170 | TAC | CCA | GGA | CAG | GCT | CCT | CCA | GGG | GGT | 196 |
| 197 | TAT | CCT | GGA | CAG | GCT | CCT | CCT | AGT | GCC | 223 |
| 224 | TAT | CCG | GGC | CCA | ACT | GGC | CCT | AGT | GCT | 250 |
| 251 | TAT | CCT | GGC | CCA | ACT | GCC | CCT | GGA | GCT | 277 |
| 278 | TAT | CCT | GGC | CCA | ACT | GCC | CCC | GGA | GCC | 304 |
| 305 | TTC | CCA | GGG | CAA | CCT | GGG GGA | CCT | GGA | GCC | 334 |
| 335 | TAC | CCC | AGT | --- | GCT | --- | CCT | GGG | GCC | 355 |
| 356 | TAC | CCC | AGT | --- | GCT | --- | CCT | GGG | GCC | 376 |
| 377 | TAT | CCT | GCT | ACT | GGC | CCC | TTT | GGT | GCC | 403 |

FIG.8B

```
         142                          167
εBP     M-LITIIGTVKPNANSITLNFKKGNDI
         : : :: :: ::: ::::::
FcγRα   MVTLMCEGTHNP-GNSSTQWFHNGRSI
         21                          46

211                                                  262
εBP     KIQVLVEADHFKVAVNDVHLLQYNHRMKNLREISQLGIIGDITLTSASHAMI
         :: :: ::  ::::::     ::: :::: ::  :: :  :::  :
FcγRα   RSQVQASYT-FKATVNDSGEYRCQMEQTRLSDPVDLGVISDWLLLQTPQRVF
         47                                                   97
```

FIG. 9B

DNA ENCODING IGE-BINDING PROTEIN WITH REPETITIVE SEQUENCE AND HOMOLOGY WITH IGG RECEPTOR

GOVERNMENT RIGHTS

This invention was made with Government support under the grants listed below. The government has certain rights in the invention:
Granting Agency: National Institutes of Health
Grant No(s): RO1 AI19747; RO1 AI27703

This invention was made with government support under Grants Nos. AI 19747 and AI 20958 awarded by the National Institutes of Health. The government has certain rights in the invention.

This is a continuation of Ser. No. 07/247,170, filed Sep. 21, 1988, which is a continuation-in-part of Ser. No. 07/726,250, Apr. 23, 1985, both of which application are now abandoned, to which priority is claimed.

FIELD OF THE INVENTION

This invention is in the field of recombinant DNA technology and more particularly to the production of IgE specific protein having an apparent molecular weight of about 31,000 daltons.

BACKGROUND OF THE INVENTION

Both the production and function of immunoglobulin E (IgE) molecules are intimately dependent on IgE-binding proteins. One type of IgE-binding protein includes the cell surface receptors of mast cells, basophils, lymphocytes and other cell types (Ishizaka, T. and Ishizaka, K., *Prog. Allergy*, 19:60-121, 1975; Froese, A., *CRC Crit. Rev. Immunol.*, 1:79-130, 1980). The receptors on mast cells and basophils are responsible for IgE-mediated immediate hypersensitivity reactions (Ishizaka, K. and Ishizaka, T., *Immunol. Rev.*, 41:109-148, 1978; Metzger, H., Alearaz, G., Hohman, R., Kinet, J.-P., Pribluda; V. and Quarto, R., *Annu. Rev. Immunol.*, 4:419-470, 1986), while those on lymphocytes play important roles in the regulation of IgE antibody responses (Spiegelberg, H. L., *Adv. Immunol.*, 35:61-88, 1984; Ishizaka, K., *Annu. Rev. Immunol.*, 2:159-182, 1984). Another type of IgE-binding protein includes the lymphokines which function in either potentiating or suppressing IgE antibody production (Spiegelberg, H. L., *Adv. Immunol.*, 35:61-88, 1984). In order to further understand the IgE system, it is important to establish the structural relatedness of these proteins, the structure-function relationship of each of these proteins, and the regulation of their gene expression. To this end, this invention's primary objective is to initiate molecular cloning of DNA for these relevant proteins.

Rat basophilic leukemia (RBL) are cells which have been used extensively to study a high affinity IgE receptor present on basophils and mast cells and from which IgE-binding proteins have already been isolated and characterized (reviewed in Ishizaka, T. and Ishizaka, K., *Prog. Allergy*, 19:60-121, 1975; Metzger, H., Alearaz, G., Hohman, R., Kinet, J.-P., Pribluda, V. and Quarto, R., *Annu. Rev. Immunol.*, 4:419-470, 1986; Katz, D. H. and Marcelletti, J. F., *Prog. Immunol. Proc. Int. Congr. Immunol.*, 5:465-482, 1983). One well-studied IgE-binding protein is a glycoprotein of $M_r=55,000$ which has been studied in a number of laboratories (Metzger, H., Kinet, J.-P., Perez, Montfort, R., Rivnay, B. and Wank, S. A., *Prog. Immunol. Proc. Int. Congr. Immunol.*, 5:493-501, 1983; Hempstead, B. L., Parker, C. W. and Kulczycki, A., Jr., *J. Biol. Chem.*, 256:10717-10723, 1981; Kulcycki, A., Jr. and Parker, C. W., *J. Biol. Chem.*, 254:3187-3193, 1979). It has been definitively established that this protein is expressed on the surface of RBL cells, mast cells and basophils, and is responsible for the high-affinity IgE-binding property of these cells.

The biochemistry of the high-affinity IgE receptor became somewhat complex when a multi-subunit nature of the receptor was revealed by the identification of other protein components in the efforts to purify the receptor from RBL cells. One group of scientists has isolated two additional proteins, $M_r=33,000$ (Hempstead, B. L., Parker, C. W. and Kulczycki, A., Jr., *Proc. Natl. Acad. Sci. U.S.A.*, 80:3050-3053, 1983; Hempstead, B. L., Kulczycki, A., Jr., and Parker, C. W., *Biochem. Biophys. Res. Commun.*, 98:815-822, 1981) and $M_r=10,000$ (Holowka, D. and Baird, B., *J. Biol. Chem.*, 259:3720-3728, 1984), in the affinity purification of IgE-receptor complexes. They also demonstrated that these two proteins could be chemically cross-linked to the $M_r=$ approximately 55,000 glycoprotein by treating RBL cells or cell lysates with bifunctional cross-linking reagents, and therefore designated them as the $\beta$ and $\gamma$ subunits, respectively, of the high-affinity IgE receptor, with the $M_r=$ approximately 55,000 glycoprotein being designated as the $\alpha$ subunit.

Holowka et al., supra, disclose a polypeptide of molecular weight of 30,000-35,000 which is complexed with a 55,000 molecular weight glycoprotein ($\alpha$ subunit) and two other smaller polypeptides ($\gamma$ subunits) to form the high-affinity receptor of immunoglobulin E (IgE) of RBL cells identified as the $\beta$ subunit of the IgE receptor. The multiple subunit configuration of the IgE receptor has been known for some time, but the exact nature of each subunit and what role it plays specifically in the receptor complex is just now being elucidated. However, it is known that the binding site for IgE is the 55,000 m.w. $\alpha$ subunit and that it is the only subunit or chain that binds IgE. The exact role of the $\beta$ subunit is not known, but it is known that it does not bind IgE independently. The 31,000 m.w. protein described herein that binds to IgE (i.e. IgE-Sepharose 4B) is, accordingly, not the $\beta$ subunit of Holowka et al. In addition, a subsequent paper (Metzger, H., Alearaz, G., Hohman, R., Kinet, J.-P., Pribludo, V. and Quarto, R., *Annu. Rev. Immunol.*, 35: 61-88, 1986) reports that the beta subunit does not contain the number of methionine residues initially considered possible by Holowka et al.

Another group of scientists has isolated a $M_r=30,000-33,000$ protein in addition to the $M_r=55,000$ glycoprotein, in the purification of RBL IgE receptor by repetitive affinity chromatography with IgE immunoadsorbent (Liu, F.-T. and Orida, N., *J. Biol. Chem.*, 259:10649-10652, 1984; Liu, F.-T., Albrandt, K., Mendel, E., Kulczycki, A., Jr., and Orida, N. K., *Proc. Natl. Acad. Sci. U.S.A.*, 82:4100-4104, 1985; U.S. patent application Ser. No. 06/726,250; Kulczycki, A., Jr., Isersky, C. and Metzger, H., *J. Esp. Med.*, 139:600-616, 1974). Although this protein shares certain similarities with the protein designated as the $\beta$ subunit, their exact relationship remains to be firmly established. Furthermore, it remained to be determined whether the isolation of either protein can be attributed to its ability to bind IgE independently. More recently, proteins of $M_r=30,000-33,000$ which are distinct from the $\beta$ subunit but which possess an IgE-binding property have been identified in RBL cells (Holowka, D. and Baird, B., *J. Biol. Chem.*, 259:3720-3728, 1984).

SUMMARY OF THE INVENTION

Recombinant DNA molecules are produced which have the translatable end-product of an apparently 31,000 dalton IgE specific protein. For molecular cloning, double-stranded cDNA was synthesized from sucrose gradient-fractionated RBL mRNA, inserted into vector plasmids and used to transform recipient host organisms. By screening transformants using a hybridization-selection/in vitro translation procedure, several clones containing cDNA which hybridized to mRNA coding for a 31,000 IgE-binding protein were identified. The DNA sequence of one of these cloned cDNAs were determined, and the amino acid sequence corresponding to the part of the protein was deduced. This cloned cDNA most likely codes for the 31,000 IgE-binding protein identified in RBL cells, which appears to be uniquely related to the IgE-binding phenotype of the cells and which may have a significant role in the IgE mediated activation of basophils and mast cells.

The invention includes a method of producing a cDNA molecule which has, as a translational product, a polypeptide which selectively binds IgE, the method comprising of isolating the genetic material coding for IgE-binding polypeptide which has a molecular weight of about 31,000 daltons, is immunoprecipitated from translational products of RBL mRNA and is not precipitated by normal rabbit serum; incorporation of the genetic material into a vector; transfer of the vector into a recipient organism; selection and cloning of the host cell carrying the IgE-binding protein expression; producing clones; and collecting the protein produced.

An IgE-binding protein produced by the aforesaid method reacts specifically with the anti-εBP antiserum and binds with IgE-Sepharose 4B.

The IgE-binding protein produced by the aforesaid method is characterized as a molecule with at least five methionine residues; a molecule which is devoid of potential N-glycosylation sites; and a molecule which can be isolated independently from a 55,000 Dalton IgE-binding protein.

The invention also includes cDNA characterized by the production of an approximately 31,000 Dalton IgE-specific binding protein.

The cDNA is characterized by the production of a translational product, wherein said translational product is: an approximately 31,000 Dalton IgE-binding protein; a molecule with at least five methionine residues: a molecule having no N-glycosylation sites; and a molecule isolated independently from a 55,000 Dalton IgE protein.

The cDNA may also be characterized by the production of an IgE-binding protein having an approximate molecular weight of about 31,000 daltons, characterized in that it is: a molecular having 262 amino acid residues; a molecule that reacts specifically with anti-εBP antiserum; and a molecule which hybridizes specifically with mRNA from RBL cells.

Figure 1A:
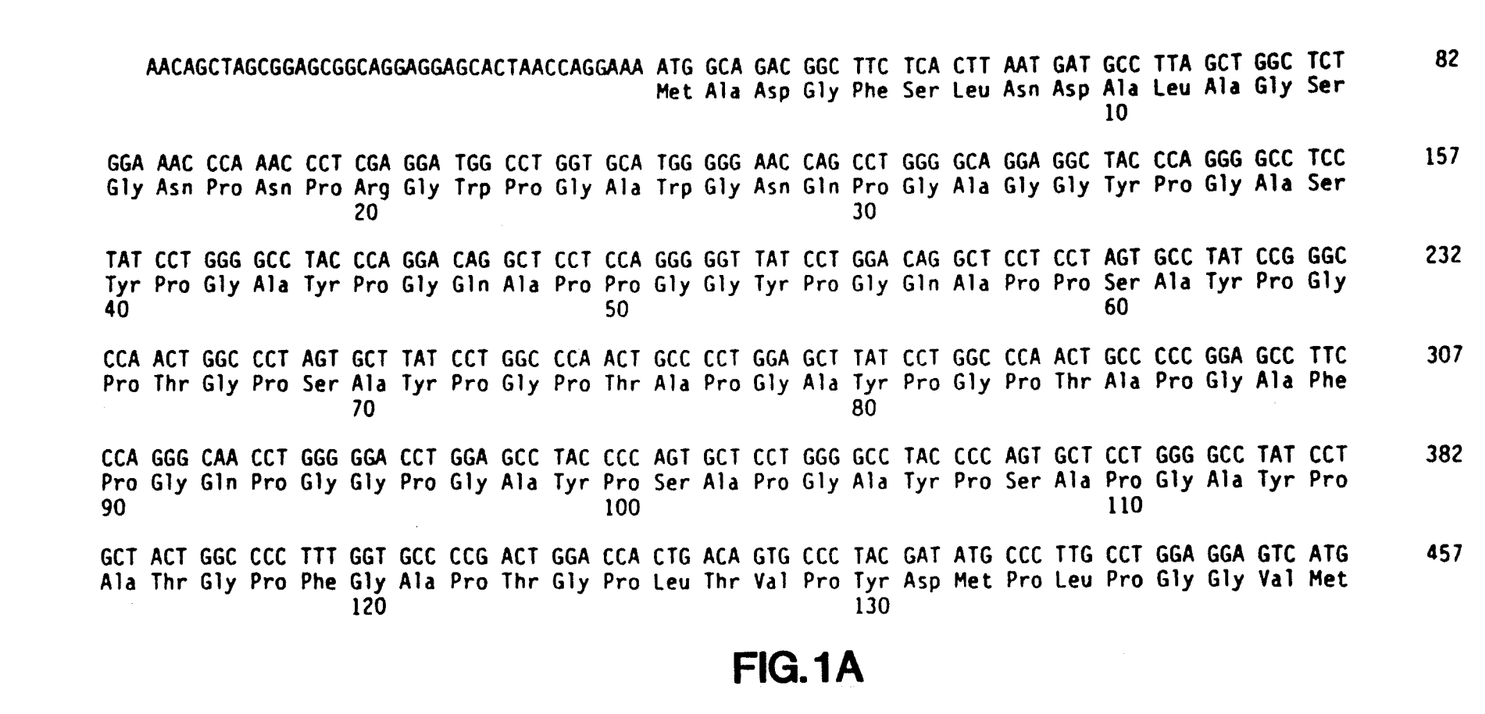
FIG. 1 is the nucleotide sequence of E8 cDNA and its deduced amino acid sequence. The deoxynucleotide numbering scheme is presented on the margin to the right and the amino acid numbering scheme is presented below the amino acid sequence.

The cDNA characterized by the production of an IgE-binding protein having an approximate molecular weight of about 31,000 daltons characterized in that said cDNA's amino acid coding sequence is substantially as shown in FIG. 1.

The cDNA molecule is also characterized by the production of an IgE-binding protein having an approximate molecular weight of about 31,000 daltons wherein said molecule reacts specifically with an RNA species from RBL cells.

The IgE-binding protein of this invention has substantially the amino acid sequence:

Met Ala Asp Gly Phe Ser Leu Asn Asp Ala Leu Ala Gly
Ser Gly Asn Pro Asn Pro Arg Gly Trp Pro Gly Ala Trp
Gly Asn Gln Pro Gly Ala Gly Gly Tyr Pro Gly Ala Ser
Tyr Pro Gly Ala Tyr Pro Gly Gln Ala Pro Pro Gly Gly
Tyr Pro Gly Gln Ala Pro Pro Ser Ala Tyr Pro Gly Pro
Thr Gly Pro Ser Ala Tyr Pro Gly Pro Thr Ala Pro Gly
Ala Tyr Pro Gly Pro Thr Ala Pro Gly Ala Phe Pro Gly
Gln Pro Gly Gly Pro Gly Ala Tyr Pro Ser Ala Pro Gly
Ala Tyr Pro Ser Ala Pro Gly Ala Tyr Pro Ala Thr Gly
Pro Phe Gly Ala Pro Thr Gly Pro Leu Thr Val Pro Tyr
Asp Met Pro Leu Pro Gly Gly Val Met Pro Arg Met Leu
Ile Thr Ile Ile Gly Thr Val Lys Pro Asn Ala Asn Ser
Ile The Leu Asn Phe Lys Lys Gly Asn Asp Ile Ala Phe
His Phe Asn Pro Arg Phe Asn Glu Asn Asn Arg Arg Val
Ile Val Cys Asn Thr Lys Gln Asp Asn Asn Trp Gly Arg
Glu Glu Arg Gln Ser Ala Phe Pro Phe Gly Ser Gly Lys
Pro Phe Lys Ile Gln Val Leu Val Glu Ala Asp His Phe
Lys Val Ala Val Asn Asp Val His Leu Leu Gln Tyr Asn
His Arg Met Lys Asn Leu Arg Glu Ile Ser Gln Leu Gly
Ile Ile Gly Asp Ile Thr Leu Thr Ser Ala Ser His Ala
Met Ile

DETAILED DESCRIPTION OF THE DRAWINGS

FIG. 5B depicts analysis results when RBL cell lysates were subjected to affinity purification with IgE-Sepharose 4B and the bound proteins were iodinated, eluted and treated with lentil lectin-Sepharose 4B. The unbound material was then i) reacted with IgE-Sepharose 4B (lane a); or ii) subjected to immunoprecipitation with rabbit anti-εBP (lane b) or normal rabbit serum (lane c). Isolated proteins were analyzed on 10% polyacrylamide gels.

FIG. 6 depicts a NaDodSO$_4$/PAGE analysis of in vitro translation products encoded by E8 cDNA. Lane a, in vitro translation mixture without exogenous mRNA added and immunoadsorbed with mouse monoclonal IgE-Sepharose 4B. Lanes b and c, in vitro translation products from E8 mRNA immunoadsorbed with mouse monoclonal IgG1-Sepharose 4B (lane b) or with mouse monoclonal IgE-Sepharose 4B (lane c). Each lane represents material eluted from the immunoadsorbent.

FIG. 7 depicts a hydropathy plot analysis of εBP. The deduced amino acid sequence of εBP encoded by cDNA clone E8 was subjected to hydropathy analysis (Hopp, T. P. and Woods, K. R., *Proc. Natl. Acad. Sci. U.S.A.*, 78:3824–3828, 1981). Positive values indicate hydrophilicity and negative values indicate hydrophobicity. Numbers at the bottom reflect the amino acid numbering scheme as in FIG. 1.

DETAILED DESCRIPTION OF THE INVENTION

This invention involves the production of an IgE-binding protein and the production of a cDNA molecule capable of use in recombinant DNA technology. More particularly, this invention involves the formation of a cDNA that produces an IgE-binding protein having an approximate molecular weight of about 31,000 daltons, and the production of host/recipient organisms which are capable of producing that protein.

Figure 2A:
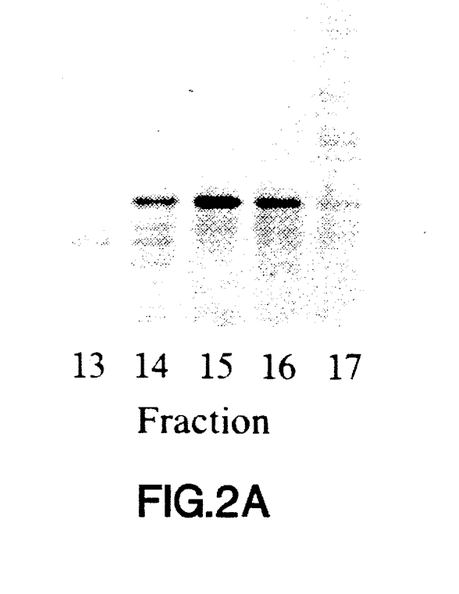
FIG. 2A is a photoradiograph are representation of NaDodSO$_4$-PAGE analysis of IgE-binding proteins isolated from the in vitro translation products of RBL mRNA. A) RBL poly(A)+ RNA was fractionated on a 10-30% sucrose gradient (see Maxam, A. and Gilbert, W., *Methods Enzymol.*, 64:499-560, 1980 for the RNA sedimentation coefficient in each fraction) and individual fractions were translated in vitro, IgE-binding proteins in the translation products were then isolated using IgE-Sepharose 4B.

Identification of 31K IgE-Binding Protein in the In Vitro Translation Product of RBL mRNA Previously, we have demonstrated the expression of IgE-binding activity on the surface of Xenopus oocytes injected with RBL mRNA and have isolated from those oocytes a 31K translation product using an IgE immunoadsorbent (Maxam, A. and Gilbert, W., *Methods Enzymol.*, 64:499–560, 1980). The extraordinary intensity of the 31K protein band on NaDodSO$_4$-PAGE gels in comparison to the presumed α subunit of the IgE receptor suggested that this protein might have an intrinsic IgE-binding activity. Sucrose gradient-fractionated RBL mRNA was subjected to in vitro translation in the rabbit reticulocyte lysate system. The translation products (composed of numerous translated proteins) were examined by affinity purification with IgE immunoadsorbent. As shown in FIG. 2A, a 31K protein was isolated virtually free of other proteins from the translation products of 13-14S RNA.

Figure 1B:
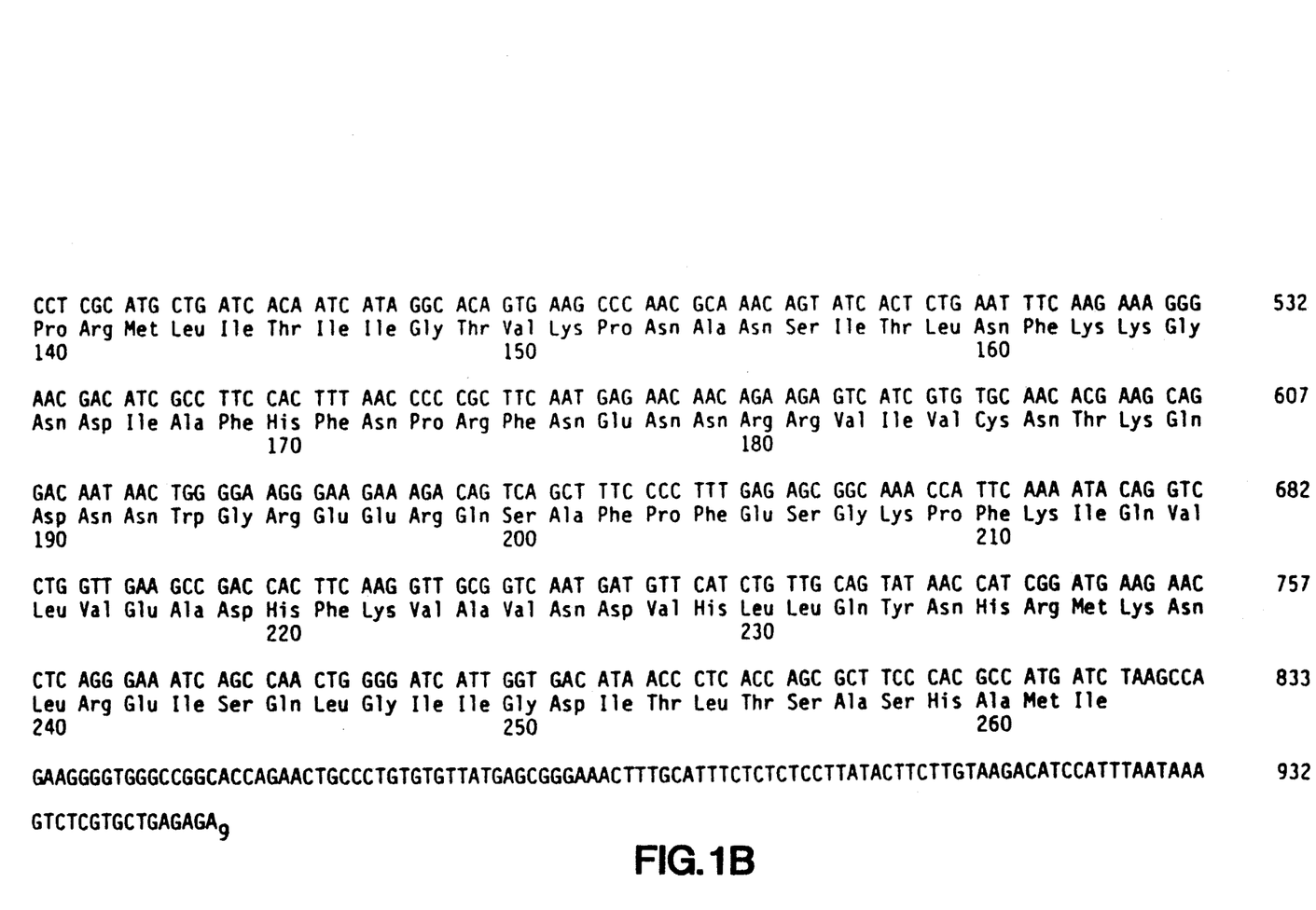
Figure 2B:
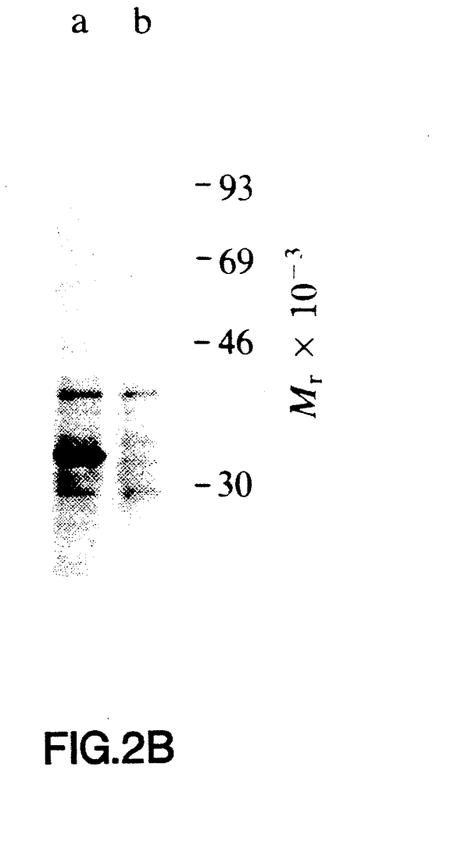
FIG. 2B depicts the results of in vitro immunoprecipitation analysis of a pool of fractions 13-16 from the fractionation that gave the results depicted in FIG. 2A. In this analysis in vitro RNA (pool of fractions 13-16) were subjected to immunoprecipitation with rabbit anti-εBP serum (lane a) or normal rabbit serum (lane b). The proteins were analyzed on 10% polyacrylamide gels.
Figure 3:
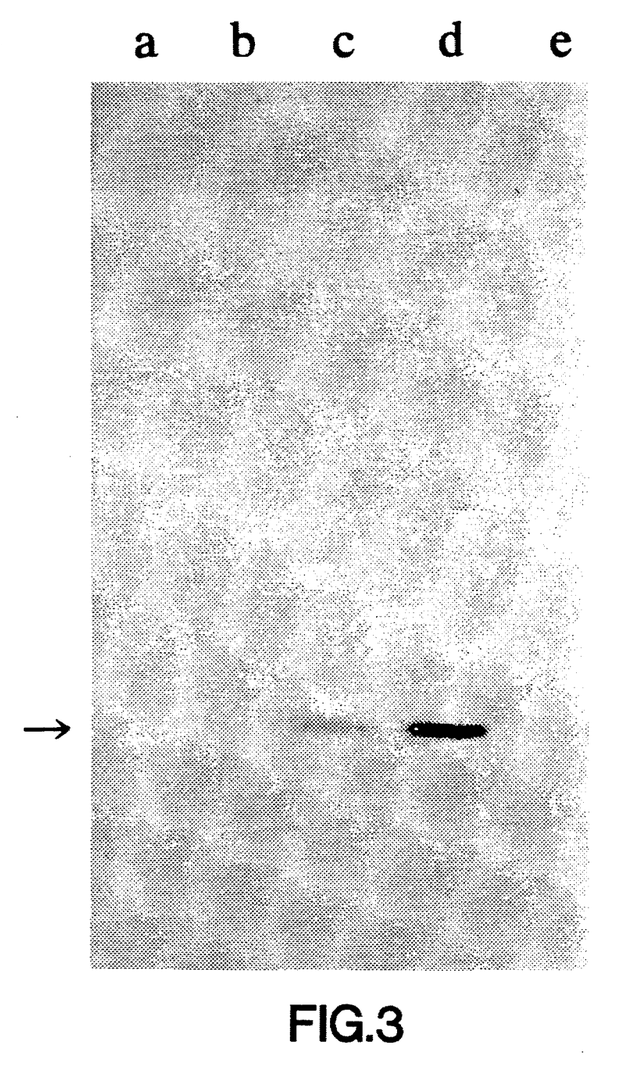
FIG. 3 is a representation of NaDodSO$_4$-PAGE analysis of the in vitro translation product from mRNA hybridized to a cloned cDNA. mRNA hybridizing with 136C9.13 cDNA immobilized on nitrocellulose filters were translated in vitro and the translation products were reacted with Sepharose 4B conjugated with BSA (lane a), mouse monoclonal IgG$_1$ (lane b) or mouse monoclonal IgE (lane c), or were subjected to immunoprecipitation with rabbit anti-εBP serum (lane d), or normal rabbit serum (lane e). Isolated proteins were analyzed on 10% polyacrylamide gels.

A $M_r$=30,000–33,000 protein, in addition to another higher molecular weight protein, was isolated from RBL cells lysates using IgE immunoadsorbent (14–16). It has been reported that polyclonal rabbit antisera raised against these proteins appeared to react with both protein components (Liu. F.-T., Albrandt, K., Mendel, E., Kulczycki, A., Jr., and Orida, N. K., *Proc. Natl. Acad. Sci. U.S.A.*, 82:4100–4104, 1985; U.S. patent application Ser. No. 06/726,250). It was postulated that the 31K protein detected above most likely corresponded to the small $M_r$=30,000–33,000 protein and that the antisera would be useful to facilitate the study of the 31K protein. Therefore, the reactivity of this translation product with the serum was examined. (For simplicity, this antisera is designated as anti-IgE binding proteins; anti-εBP). As shown in FIG. 1B, a 31K protein was immunoprecipitated from the translation products of RBL mRNA by anti-εBP). As shown in FIG. 2B, a 31K protein was immunoprecipitated from the translation products of RBL mRNA by anti-εBP serum (lane a) and not by normal rabbit serum (lane b). It should be noted that the 31K protein band is clearly the major protein in immunoprecipitated and is the only protein which was immunoprecipitated specifically.

Cloning of cDNA Coding for the 31K IgE-Binding Protein

Figure 4:
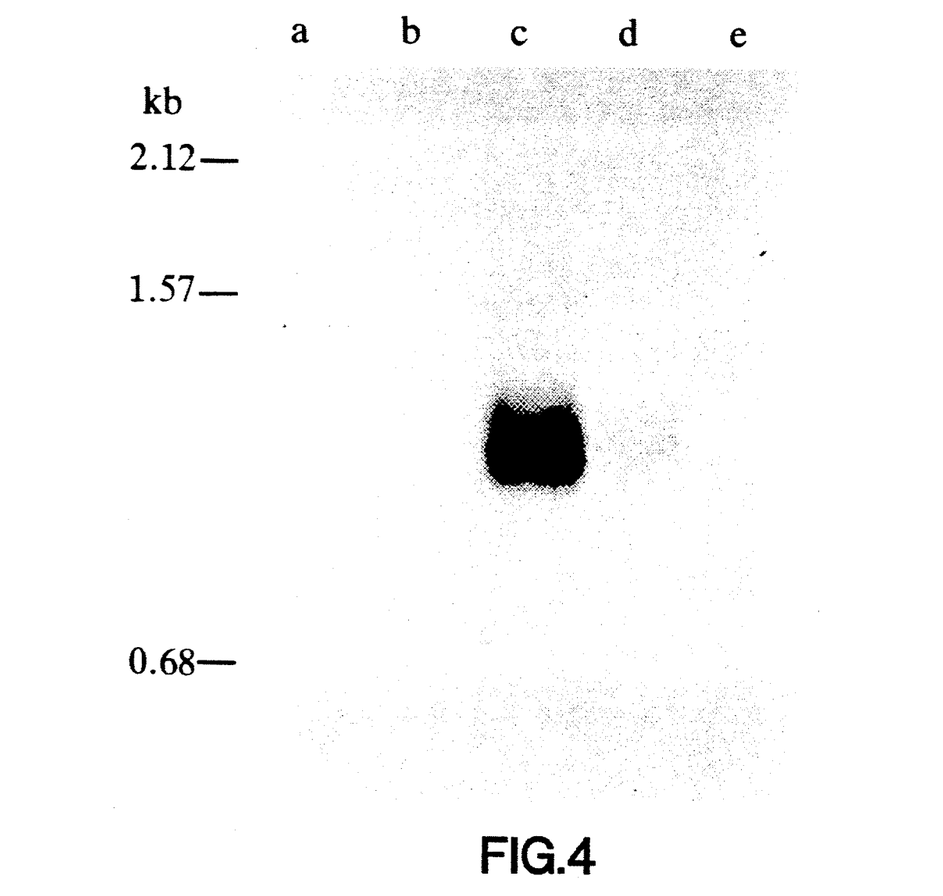
FIG. 4 is a reproduction of northern blot hybridization analysis of RNA from various cells lines with cloned 136C9.13 cDNA probe. Total poly(A)+ RNA (5 μg each) from five cell lines—a mouse IgE-secreting hybridoma (26.82, lane a), a mouse IgG$_1$—secreting hybridoma (109.3, lane b), RBL (lane c), mouse mastocytomas P815 (lane d) and rat lymphoma IR983F (lane e) were glyoxylated, electrophoresed on 2% agarose gels, transferred to nitrocellulose filters and hybridized with $^{32}$P-labeled 136C9.13 probe. Hybridization conditions: 2×Denhardts/25 mM PIPES, pH 6.8/25 mM EDTA/0.75M NaCl/50% formamide/0.2% NaDodSO$_4$/50 μg/ml heat-denatured tRNA/50 μg/ml heat-denatured salmon sperm DNA; 42° C., 16 hr. Washing conditions: 15 mM NaCl/1.5 mM Na citrate/0.1% NaDodSO$_4$ at 51° C.

RBL mRNA from sucrose density gradient fractions 14–16 was used to generate a cDNA library which was screened by a hybridization-selection/in vitro IgE-binding protein. From about 1000 clones, one positive clone (136C9.13) was identified. As shown in FIG. 4, cDNA from this clone hybridized to mRNA from RBL cells which could be translated to a 31K protein which binds IgE (lane c) but not BSA (lane a) or IgG$_1$ (lane b). Furthermore, the translated protein was shown to react specifically with the anti-εBP antiserum (lane d vs. lane c). Insert analysis indicated that the cloned cDNA was about 570 bp in length.

The nucleotide sequence of the 136C9.13 cDNA was determined and a single open reading frame was identified. As shown in FIG. 1, this cDNA contains a coding sequence for 138 amino acids representing approximately the corboxy-terminal half of the protein. The cDNA sequence also contains 121 nucleotides of 3' untranslated region and a typical AATAAA sequence fifteen to twenty-one bases before the poly(A) addition site. Homology searches of the nucleic acid database demonstrated that this sequence has not been previously described and that there i no significant homology to other known protein or DNA sequences. The protein appears rather hydrophilic as indicated by a hydropathicity plot (Lewis, V. A., Koch, T., Plutner, H. and Mellman, I., *Nature (London)*, 324:372-375, 1986); inspection of the sequence does not identify any potential transmembrane sequences nor any N-linked carbohydrate attachment sites.

The 31K IgE-Binding is Expressed Uniquely by RBL Cells and Not by Cells Lacking Receptors In order to relate the 136C9.13 cDNA to the IgE-binding property of RBL cells with confidence, one should first demonstrate that this cDNA detects a mRNA species present in RBL cells but not in other cells which lack the IgE receptor. Northern blot hybridization experiments were performed, the results of which are shown in FIG. 4. The 136C9.13 cDNA hybridized specifically with mRNA of sizes 1.1 kb and 1.6 kb from RBL cells (lane c). Under more stringent conditions, only the 1.1 kb mRNA band was detected. The 1.1 kb band but not the 1.6 kb band was also detected with much lower intensity in mRNA from mouse mastocytoma line P815 (lane d). Neither or these two mRNAs were found in a rate lymphoma (lane c) nor in either of two mouse hybridomas secreting IgE (lane a) and IgG$_1$ (lane b), respectively. A 1.1 kb mRNA ha also been detected in mouse mastocytomas cell line CXBG ABMCT-1 but not in mouse macrophage line P388D1 (data not shown).

Figure 5A:
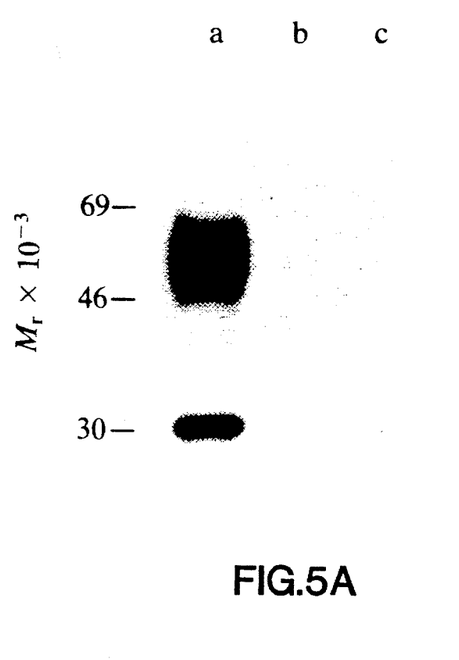
FIGS. 5A and 5B are a representation of NaDodSO$_4$-PAGE analysis of $^{125}$I-labeled IgE-binding protein from RBL cells depicting cell lysates from RBL (lane a), P815 (lane b) or rat lymphoma (lane c) were subjected to repetitive affinity purification with IgE-Sepharose 4B as described in Example 1. The proteins were labeled with $^{125}$I at the end of the first cycle of affinity purification.

The discovery of an RBL mRNA coding for a 31K IgE-binding protein prompted us to document that this protein was actually translated in vivo in certain cell types which bind IgE. When an RBL cell lysate was adsorbed with IgE-Sepharose and the bound proteins were iodinated, eluted and readsorbed with IgE-Sepharose, a 31 K protein was indeed isolated in addition to a protein of $M_r = \sim 55,000$ which has been designated as the α subunit of the IgE receptor (FIG. 5, lane a). The two-cycle affinity purification procedure was found to be necessary to eliminate proteins binding to IgE nonspecifically (Liu. F.-T. and Orida, N., *J. Biol. Chem.*, 259:10649-10652, 1984; Liu, F.-T., Albrandt, K., Mendel, E., Kulczycki, A., Jr., and Orida, N. K., *Proc. Natl. Acad. Sci. U.S.A.*, 82:4100-4104, 1985; U.S. patent application Ser. No. 06/726,250 now abandoned). It was convenient, in conjunction with this procedure, to radiolabel the protein at the end of the first cycle of affinity purification, yielding proteins of high specific radioactivity. Neither protein was isolated from mouse mastocytoma P815 cells (lane b) nor from rate B lymphoma cells (lane c), indicating that both proteins are unique to RBL cells.

Figure 5B:
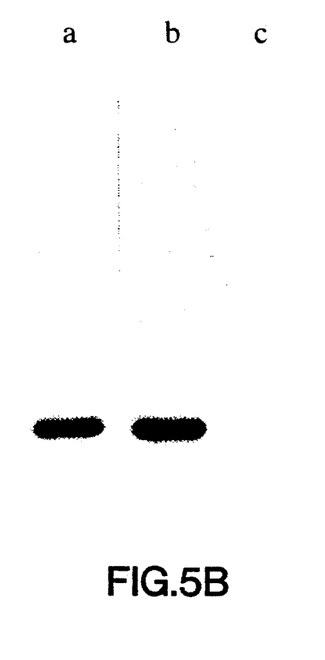

Next, it was desired to establish that the RBL cell-derived 31K protein detected above is an IgE-binding protein. Since it may be argued that in the above experiments, the 31K protein was isolated from RBL cells by virtue of its association with the $M_r = \sim 55,000$ $M_r$ protein, it is necessary to demonstrate that this protein can be isolated independently from the high molecular weight component. This was approached by employing a lectin adsorbent since the latter protein (α subunit), which is highly glycosylated, in known to bind to various lectins (Helm, R. M., Conrad, D. H. and Froese, A., *Int. Arch. Allergy Appl. Immunol.*, 58:90-98, 1979), while the 31K protein, which is not (or lightly) glycosylated should bind to lectins only weakly or not at all. Thus, the protein bound to and subsequently eluted from the first IgE-Sepharose 4B described above was allowed to react with lentil lectin-Sepharose 4B and the unbound material was then treated with IgE immunoadsorbent. As shown in FIG. 5B (lane a), the 31K protein was indeed the major protein isolated by IgE-Sepharose 4B. This result indicates that the 31K protein found in RBL cells is an IgE-binding protein.

The success of the above experiment also established that the isolated 31K protein, alone, reacts with the anti-εBP antiserum, as is the case for the in vitro translated 31K protein. Thus, supernatants obtained following the absorption with lentil lectin-Sepharose 4B described above were subjected to immunoprecipitation with anti-εBP serum, and the 31K protein was found to be specifically immunoprecipitated (FIG. 5B, lane b vs. lane c). This result strongly supports the relatedness of this protein to the one identified in the in vitro translation products.

EXAMPLE 1

The example of the invention is divided into the following stages:
I. Preparation of RNA and in vitro translation of RNA.
II. cDNA cloning and screening.
III. Immunoprecipitation.
   (A) Isolation of an IgE-binding protein with IgE-Sepharose 4B; one cycle procedure used for in vitro translation products.
   (B) Isolation of an IgE-binding protein by repetitive affinity purification with IgE-Sepharose 4B; used to cell lysates.
   (C) Immunoprecipation with rabbit anti-εBP serum.
   (D) Electrophoresis, northern blot hybridization and DNA sequence analysis.

Cell Lines and Reagents

Cell lines used include RBL (Kulczycki, A., Jr., Isersky, C. and Metzger, H., *J. Exp. Med.*, 139:600-616, 1974), mouse mastocytoma P815 (Dunn, T. B. and Potter, M., *J. Natl. Cancer Inst.*, 18:587-595, 1957), rat lymphoma IR983F (Bazin, H. in *Protides of the Biological Fluids. 29th Colloquium* 1981, ed. Peeters, H. (Pergamon, Oxford), p. 615-618), and mouse hybridomas secreting either antidinitrophenyl (DNP) IgE or IgG$_1$ (Liu, F.-T., Bohn, J. W., Ferry, E. L., Yamamoto, H., Hominaro, C. A., Sherman, K., Klinman, N. R. and Katz, D. H., *J. Immunol.*, 124:2728-2738, 1980). Mouse monoclonal IgE (III-DNP-ε-26.82) and IgG$_1$ (III-DNP-α1-109.3) specific for DNP and rabbit antiserum prepared against proteins affinity-purified from RBL cells by repetitive chromatography on IgE immunoadsorbent (anti-εBP; Hempstead, B. L., Parker, C. W. and Kulczycki, A., Jr., *J. Biol. Chem.*, 256:10717-10723, 1981) have been described previously. Immunoadsorbents were prepared by conjugating 10 mg of protein to 1 g (dry weight) of CNBr-activated Sepharose 4B (Pharmacia).

Preparation of RNA and In Vitro Translation of RNA

Extraction of total cytoplasmic RNA from various cell sources by the standard phenol/chloroform method, isolation of poly(A)+ RNA by oligo(dT)-cellulose affinity chromatography and sucrose density gradient fractionation of RBL poly(A)+ RNA have all been described (Liu, F.-T. and Orida, N., *J. Biol. Chem.*, 259:10649–10652, 1984). In vitro translation of mRNA was performed using the rabbit reticulocyte lysate system (New England Nuclear) in the presence of [$^{35}$S]methionine.

cDNA Cloning Screening and Sequencing

Double-standard cDNA was prepared from sucrose gradient-fractionated RBL mRNA, inserted into the Pst I site of pBR322 and used to transform *E. coli* C600 (Liu, F.-T., Albrandt, K., Sutcliffe, J. G. and Katz, D. H., *Proc. Natl. Acad. Sci. U.S.A.*, 79:7852–7856, 1982). A hybridization-selection/in vitro translation procedure was used to screen for positive clones (Parnes, J. R., Velan, B., Felsenfeld, A., Ramanathan, L., Ferini, U., Appella, E. and Seidman, J. G., *Proc. Natl. Acad. Sci. U.S.A.*, 79:2253–2257, 1981). Briefly, pools of twelve chimeric plasmids were bound to nitrocellulose filters, the filters were incubated with total RBL poly (A)+ RNA and the hybridized RNA was eluted and translated in vitro. The translation products were subjected to immunoprecipitation (see below) to detect an IgE-binding protein.

A cDNA library designed for the preferential cloning of full-length molecules was prepared as described (Okayama, H. and Berg. P., *Mol. Cell. Biol.*, 2:161–170, 1982) from sucrose gradient-fractionated RBL cell mRNA. *E. coli* C600 transformants were screened by colony hybridization (Hanahan, D. and Meselson, M., *Gene*, 10:63–67, 1980) with the $^{32}$P-labeled nick-translated 575-base-pair (bp) Pst I fragment of clone 136C9.13 encoding the partial nucleotide sequence of εBP. The cell line 136C9.13 was deposited with the American Type Culture Collection, 12301 Parklawn Drive, Rockville, Md. U.S.A. (ATTC) Apr. 23, 1985 and was assigned Accession No. 53107 by the ATCC. The deposit was made pursuant to the provisions of the Budapest Treaty respecting microbiological deposits and under the conditions provided for under ATCC's agreement for Culture Deposit for Patent Purposes, which assures that this deposit will be made available to the U.S. Commissioner of Patents and Trademarks pursuant to 35 U.S.C. 122 and 35 C.F.R. 1.14, and will be made available to the public upon issue of a U.S. Patent which requires that such deposit be maintained. Applicant agrees to renew the deposit if necessary to assure availability for a period of at least thirty years from the date of deposit. The availability of this deposit is not to be construed as a license to practice the invention in contravention of the rights under the authority of any government in accordance with its patent laws. Hybridization was performed in 0.3M sodium chloride/0.03M sodium citrate, pH 7.0/5x Denhardt's solution/10 mM EDTA/0.1% NaDodSO$_4$/100 μg of heat-denatured sonicated salmon sperm DNA per ml of 65° C. followed by washing in 0.03M sodium chloride/0.003M sodium citrate, pH 7.0/01% NaDodSO$_4$ at 65° C. and autoradiography (1x Denhardt's solution is 0.02% bovine serum albumin/0.02% Ficoll/0.02% polyvinylpyrrolidone). One strongly hybridizing clone (E8) was isolated from approximately 6800 transformants screened, and its DNA sequence was determined by employing both the dideoxy chain-termination method (Sanger, E., Nicklen, S. and Coulson, A. R., *Proc. Natl. Acad. Sci. U.S.A.*, 74:5463–5467, 1977) and the chemical cleavage procedure (Maxam, A. and Gilbert, W., *Methods Enzymol.*, 64:499–560, 1980).

In Vitro Transcription and Translation

The Pst I-Pvu II fragment from clone E8 encompassing the entire cDNA sequence, was inserted into the M13 polylinker site of a modified pSP6 vector (Melton, D. A., Krieg, P. A., Rebagliati, M. R., Maniatis, T., Zinn, K. and Green, M. R., *Nucleic Acids Res.*, 12:7035–7056, 1984) (pSP64; Promega Biotec, Madison, Wis.). Plasmid DNA, prepared by standard methods, was linearized and used as a template to synthesize capped mRNA in vitro (Riboprobe System; Promega Biotec). The E8 mRNA was then translated in vitro, using [$^{35}$S]methionine in a rabbit reticulocyte lysate system (New England Nuclear). The translation products were subsequently immunoadsorbed with mouse monoclonal IgG1-Sepharose 4Bor mouse monoclonal IgE-Sepharose 4B as described (Liu, F.-T., Albrandt, K., Mendel, E., Kulczycki, A., Jr., and Orida, N. K., *Proc. Natl. Acad. Sci. U.S.A.*, 82:4100–4104, 1985; U.S. patent application Ser. No. 06/726,250 now abandoned), and materials eluted from the immunoadsorbents were analyzed by NaDodSO$_4$/PAGE (Laemmli, U.K., *Nature (London)*, 227:680–685, 1970), and fluorographed (EN$^3$HANCE; New England Nuclear).

Immunoprecipitation (A) Isolation of an IgE-Binding Protein with IgE-Sepharose 4B; One Cycle Procedure Used for In Vitro Translation Products. The translation mixture (20 μl) was diluted with an equal volume of 2×TENT (1×TENT=20 mM Tris-HCl, pH 7.5/10 mM EDTA/150 mM NaCl/1% Trasylol) containing 2% Triton X-100 and mixed with 50 μl (packed volume) of rabbit gamma-globulin (RγG)-Sepharose 4B for one hour at 4° C. The supernatant was then mixed with 50 μl of IgE-Sepharose 4B for four hours at 4° C. The beads were washed four times with 4 ml of TENT-1% Triton X-100, and one time with 4 ml of TENT-0.05% NaDodSO$_4$. The bound protein was eluted with 75 μl of 62.5 mM Tris-HCl, pH 6.8/2% NaDodSO$_4$ glycerol/5% 2-mercaptoethanol by boiling for three minutes.

(B) Isolation of an IgE-Binding Protein by Repetitive Affinity Purification with IgE-Sepharose 4B; Used for Cell Lysates. This procedure is essentially the same as previously reported (Liu, F.-T. and Orida, N., *J. Biol. Chem.*, 259:10649–10652, 1984; Liu, F.-T., Albrandt, K., Mendel, E., Kulczycki, A., Jr., and Orida, N. K., *Proc. Natl. Acad. Sci. U.S.A.*, 82:4100–4104, 1985; U.S. patent application Ser. No. 06/726,250 now abandoned) with slight modifications as described (Maxam, A. and Gilbert, W., *Methods Enzymol.*, 64:499–560, 1980), hereby incorporated by reference. Briefly, the cell lysate (typically 5×10$^7$ cells) was subjected to the first cycle of affinity purification as described in (A), and the bound proteins were eluted three times each with 200 μl of 2M Tris-HCl, pH 8.8/1 Triton X-100 and subjected to a second cycle of affinity purification. In this study, at the end of the first cycle of affinity purification, proteins were radiolabeled while still bound to IgE-Sepharose 4B by the chloramine-T method (Kozak, M., *Cell*, 44:283–292, 1986) using 1 mCi of Na$^{125}$I and 10 μg of chloramine-T in 30 μl of 0.1M sodium phosphate, pH 7.5, for sixty seconds at 4° C. The beads were further washed three times with 4 ml of TENT-1% Triton X-100 and the bound proteins were eluted as described above.

(C) Immunoprecipitation with Rabbit Anti-εBP Serum. To in vitro translation products (20 μl) or proteins isolated from RBL cells using IgE-Sepharose 4B (200 μl) were added 3 μl of normal rabbit serum (NRS). The mixture was incubated for one hour and then reacted with GARG-Sepharose 4B (50 μl) for one hour. The supernatants were reacted with 3 μl of rabbit anti-εBP serum for one hour and next mixed with GARB-Sepharose 4B (50 μl) for one hour. The beads were washed and the bound proteins were eluted as described above. All the above procedures were performed at 4° C.

(D) Adsorption with Lentil Lectin-Sepharose 4B. Proteins bound to IgE-Sepharose 4B, iodinated and eluted as described in procedure (B) above were mixed with lentil lectin-Sepharose 4B (Pharmacia, 100 μl of a 1:1 suspension in 10 mM Tris-HCl, pH 7.4/0.15M NaCl/1 Triton X-100) for one hour at 4° C.

(E) Electrophoresis, Northern Blot Hybridization and DNA Sequence Analysis. NaDodSO$_4$/polyacrylamide gel electrophoresis analysis of proteins was conducted using the Laemmli system (Laemmli, U.K., *Nature (London)*, 227:680–685, 1970) hereby incorporated by reference. Gels containing $^{35}$S-labeled proteins were treated with autoradiography enhancer (EN$^3$HANCE, New England Nuclear), dried and fluorographed; gels containing $^{125}$I-labeled proteins were dried and autoradiographed. For northern blot analysis, RNAs were glyoxylated, electrophoresed on 2% agarose gels, transferred to nitrocellulose filters and hybridized with cDNA probe labeled with $^{32}$p by nick-translation (Thomas, P. S., *Proc. Natl. Acad. Sci. U.S.A.*, 77:5201–5205, 1980) hereby incorporated by reference. The DNA sequence was determined by the dideoxy primer-extension method (Sanger, F., Nicklen, S. and Coulson, A. R., *Proc. Natl. Acad. Sci. U.S.A.*, 74:5463–5467, 1977).

Identification of a Full-Length cDNA Coding for εBP.

Our previously identified cDNA (136C9.13) encoding the partial nucleotide sequence of εBP (Liu, F.-T., Albrandt, K., Mendel, E., Kulczycki, A., Jr., and Orida, N. K., *Proc. Natl. Acad. Sci. U.S.A.*, 82:4100–4104, 1985; U.S. patent application Ser. No. 06/726,250 now abandoned) was used as probe to screen an RBL cell cDNA library. One clone (E8) hybridized strongly with this probe and was identified as a full-length sibling of the 136C9.13 probe by DNA sequence analysis. The complete nucleotide sequence of the E8 cDNA and its deduced amino acid sequence are presented in FIG. 1. Amino acids 125–262 correspond to the amino acid sequence disclosed in U.S. application Ser. No. 06/726,250 to which priority is claimed. It consists of forty nucleotides of 5' untranslated sequence, an open reading frame of 786 nucleotides coding for 262 amino acids, and 121 nucleotides of 3' untranslated sequence. The methionine residue at nucleotide positions 41–43 was chosen as the initiation residue on the basis of its flanking consensus initiation sequence (A/GNN-ATG-G) (Kozak, M., *Cell*, 44:283–292, 1986) and its prediction of a 27,573-Da protein. Inspection of the sequence also reveals a typical AATAAA consensus sequence 15–21 nucleotides before the poly(A) addition site and no potential N-linked carbohydrate attachment sites (Asn-Xaa-Ser/Thr).

Figure 6:
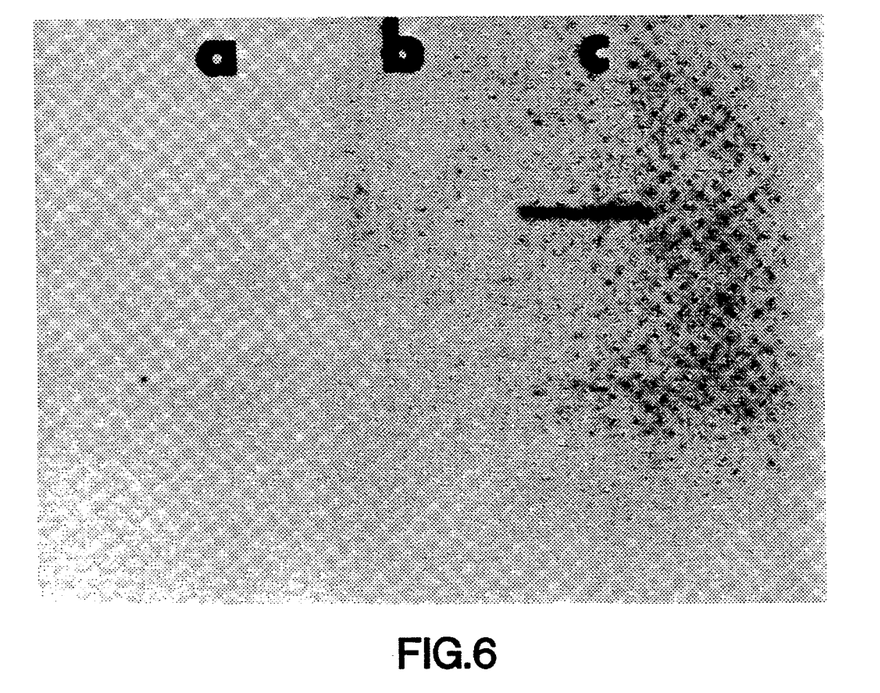

To demonstrate that clone E8 actually encodes εBP, mRNA was synthesized in vitro from E8 cDNA using the SP6 bacteriophage promoter and then translated in vitro. A translation product of $M_r$ 28,500 was specifically immunoadsorbed by IgE but not by IgG1 (FIG. 6).

Analysis of the Deduced Amino Acid Sequence of εBP.

Figure 7:
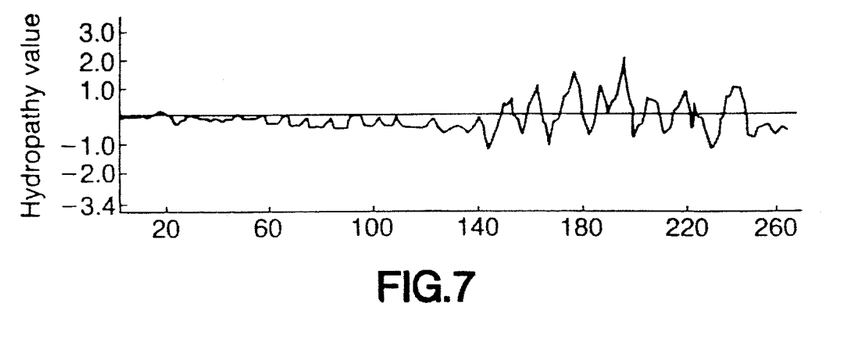

A hydropathy analysis (Hopp, T. P. and Woods, K. R., *Proc. Natl. Acad. Sci. U.S.A.*, 78:3824–3828, 1981) of εBP (FIG. 7) clearly indicates a two-domain structure. The carboxyl-terminal domain (amino acids 141–262) contains both hydrophilic and hydrophobic regions, typical or globular proteins. In striking contrast, the amino-terminal domain (amino acids 1–140) is distinct and exhibits neither a highly hydrophilic nor a hydrophobic nature. No potential membrane-spanning region was predicted by hydropathy analysis (Kyte, J. and Doolittle, R. F., *J. Mol. Biol.*, 157:105–132, 1982) nor is there a hydrophobic signal sequence at the amino terminus.

The amino acid compositions of the two domains of εBP are also dissimilar. The majority of the amino-terminal domain is composed of proline (26%), glycine (23%), and alanine (16%), whereas these residues make up only 3%, 5%, and 6% respectively, of the carboxyl-terminal domain. In addition, the carboxyl-terminal domain is highly charged, whereas the amino-terminal domain consists almost exclusively of neutral residues.

Figure 8A:
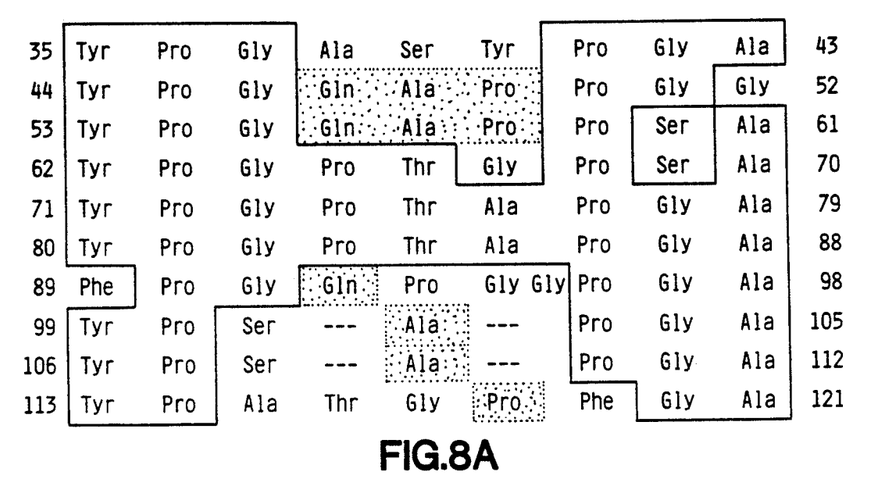
FIG. 8A depicts the amino-terminal domain of εBP showing a highly conserved repetitive sequence and demonstrating that the continuous amino acid sequence from residues 35 through 121 in the amino-terminal domain of εBP is composed of a nine-amino acid segment repeated ten times in succession. Spaces have been inserted to maximize the homology. Numbers in the margins indicate the amino acid residue numbering scheme as in FIG. 1.
Figure 8B:
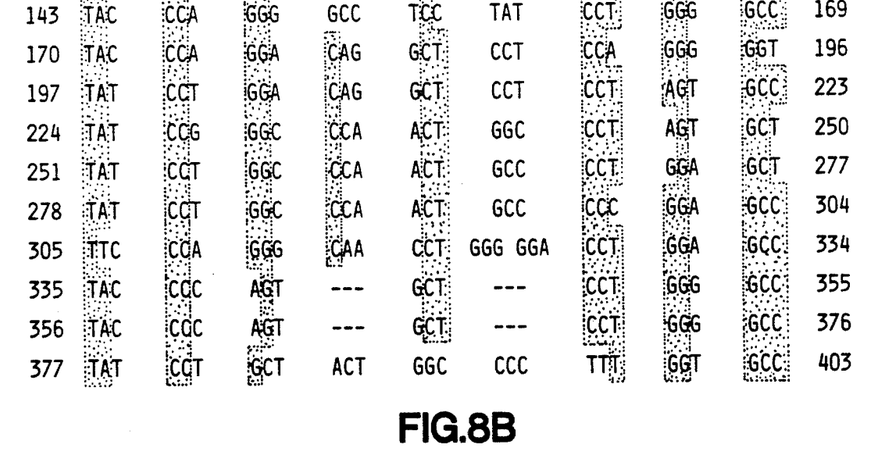
FIG. 8B depicts the corresponding nucleotide sequence of the amino acid sequence in A. Numbers in the margins indicate the nucleotide numbering scheme as in FIG. 1.

FIG. 8A illustrates another unique structural feature of εBP. The majority of the amino-terminal domain is composed of a highly conserved sequence of nine amino acids residues repeated ten times in succession. The consensus sequence for this repetitive segment is Tyr-Pro-Gly-Pro/Gln-Ala/Thr-Pro/Ala-Pro-Gly-Ala. As expected, there is a conserved nucleotide sequence corresponding to this amino acid segment, especially in the first and second codon positions (FIG. 8B). No such repetitive sequence is found in the carboxyl-terminal domain.

εBP Shares Homology with an FcγR

Recently, several groups reported the cloning and sequencing of macrophage/lymphocyte FcγR (Hibbs, M. L., Walker, I. D., Kirszbaum, L., Pietersz, G. A., Deacon, N. J., Chambers, G. W., McKenzie, I. F. C. and Hogarth, P. M., *Proc. Natl. Acad. Sci. U.S.A.*, 83:6980–6984, 1986; Lewis, V. A., Koch, T., Plutner, H. and Mellman, I., *Nature (London)*, 324:372–375, 1986; Ravetch, J. V., Luster, A. D., Weinshank, R., Kochan, J., Pavlovee, A., Portnoy, D. A., Hulmes, J., Pan. Y.-C. E. and Unkeless, J. C., *Science*, 234:718–725, 1986). This receptor is composed of two homologous domains, $\alpha_1$ and $\alpha_2$. We found εBP contains two areas with significant sequence homology to the $\alpha^1$ domain of FcγR: one area with 38% identity over twenty-six amino acids and another area with 25% identity over fifty-two amino acids (FIGS. 8A and 8B). The statistical significance of the alignments was evaluated by using the program IALIGN (National Biomedical Research Foundation, Washington, D.C.). The twenty-six-amino acid segment had an optimized score of 4.95 SD above the mean and the fifty-two-amino acid segment scored 6.86 above the mean. Thus, with the exception of th amino acids 168–210 in εBP, the entire carboxyl-terminal domain of εBP and the $\alpha_1$ domain of FcγR share homology. Approximately 65% homology exists between these areas if conservative amino acid replacements are also considered (FIG. 9).

As demonstrated, as IgE-binding protein from RBL cells with an unusual structure has been discovered and isolated. The protein contains two distinct structural domains: the amino-terminal domain is composed of a highly conserved repetitive sequence, while the carboxyl-terminal domain shares significant sequence homology with a domain of mouse FcγR.

We are certain that cDNA clone E8 codes for εBP. Previously (Liu, F.-T., Albrandt, K., Mendel, E., Kulczycki, A., Jr., and Orida, N. K., *Proc. Natl. Acad. Sci. U.S.A.*, 82:4100–4104, 1985; U.S. patent application Ser. No. 06/726,250 now abandoned), we employed a hybridization-selection/in vitro translation procedure which showed that a sibling of this cDNA hybridizes to an RBL cell mRNA that is translated in vitro to a $M_r$ 31,000 protein specifically reactive with both IgE and a specific antiserum raised against proteins (including the $M_r$ 31,000 protein) affinity-purified from RBL cells on IgE immunoadsorbent. We have further substantiated this relationship by demonstrating that E8 cDNA is transcribed and translated in vitro to a protein of a similar molecular weight, specifically reactive with IgE but not with IgG1.

We have previously demonstrated by northern blot analysis (Liu, F.-T., Albrandt, K., Mendel, E., Kulczycki, A., Jr., and Orida, N. K., *Proc. Natl. Acad. Sci. U.S.A.*, 82:4100–4104, 1985; U.S. patent application Ser. No. 06/726,250) that εBP cDNA hybridizes with RBL cell mRNA but not with mRNA from cell lines lacking εBP. In addition, antibody generated against a peptide predicted form the εBP nucleotide sequence was found to be specifically reactive with a $M_r$ 31,000 protein from RBL cells by immunoblot analysis. These results further support that the cDNA reported here corresponds to the IgE-binding protein previously identified.

One feature which makes εBP unique is the repetitive amino acid sequence comprising its amino-terminal domain. Computer search of the National Biomedical Research Foundation protein data base indicated that this repetitive sequence had not been found in any protein sequence reported as of Sep. 3, 1986. This sequence shares some similarities with collagen in that it has a high number of proline, glycine and alanine residues (Miller, F. J., in *Connective Tissue Biochemistry*, eds. Piez, K. A. and Reddi, A. H. (Elsevier, Amsterdam), pp. 41–81, 1983). However, εBP does not meet the exact structural criterion of collagen, i.e., a glycine residue at every third position, necessary for the formation of a triple helix. The abundance of proline residues and the repeated sequences in this domain suggest multiple turns and a possible recurrent folding structure for εBP. These features might also account for the discrepancy between the predicted molecular weight (27,573) and the apparent molecular weight of the purified protein as estimated from NaDodSO4/PAGE (31,000).

An additional characteristic that makes εBP interesting is its sequence homology with FcγR, suggesting that parts of the two proteins are derived from the same ancestral gene. We do not know as yet whether the areas of homology represent those responsible for binding to the respective immunoglobulin or for some other possible effector functions shared by the two proteins. In the former case it seems reasonable that a significant divergence in structure is required for two related proteins to recognize two diverging members of the immunoglobulin family. In fact, the degree of sequence homology between the specified areas of εBP and FcγR is consistent with that between the constant regions of IgE and IgG (Ishida, N., Ueda, S., Hayashida, H., Miyata, T. and Honjo, T., *EMBO J.* 1:1117–1123, 1982). It should be noted that several structural features distinguish the carboxyl-terminal domain of εBP from the α domain of FcγR. Second, εBP lacks any carbohydrate attachment sites.

The genes encoding two other proteins with an IgE-binding property have recently been cloned: human lymphocyte IgE receptor (FcεR) (Kikutani, H., Inui, S., Sato, R., Barsumian, E. L., Owaki, H., Yamasaki, K., Kaisho, T., Uchibayashi, N., Hardy, R. R., Hirano, T., Tsunasawa, S., Sakiyama, F., Suemura, M. and Kishimoto, T., *Cell*, 47:657–665, 1986; Ikuta, K., Takani, M., Kim, C. W., Honjo, T., Miyoshi, T., Tagaya, Y., Kawabe, T. and Yodoi, J., *Proc. Natl. Acad. Sci. U.S.A.*, 84:819–823, 1987) and rat IgE-binding factor (Martens, C. L., Huff, T. F., Jardieu, P., Trounstine, M. L., Coffman, R. L., Ishizaka, K. and Moore, K. W., *Proc. Natl. Acad. Sci. U.S.A.*, 82:2460–2464, 1985).

Sequence comparison revelaed that neither of these proteins shares homology with εBP or with each other. It is interesting that three different proteins, each exhibiting the functional ability to bind IgE, share no homology at the primary amino acid sequence level. This may reflect their restricted ability to recognize specific domains or distinct secondary and/or tertiary structures of the large IgE molecule. It certainly underscores the diversity inherent in the IgE system; each of these IgE-binding proteins needs to encompass amino acid sequences responsible for their varied and individual effector functions and, hence, a diversity in their primary amino acid sequence is expected.

Figure 9A:
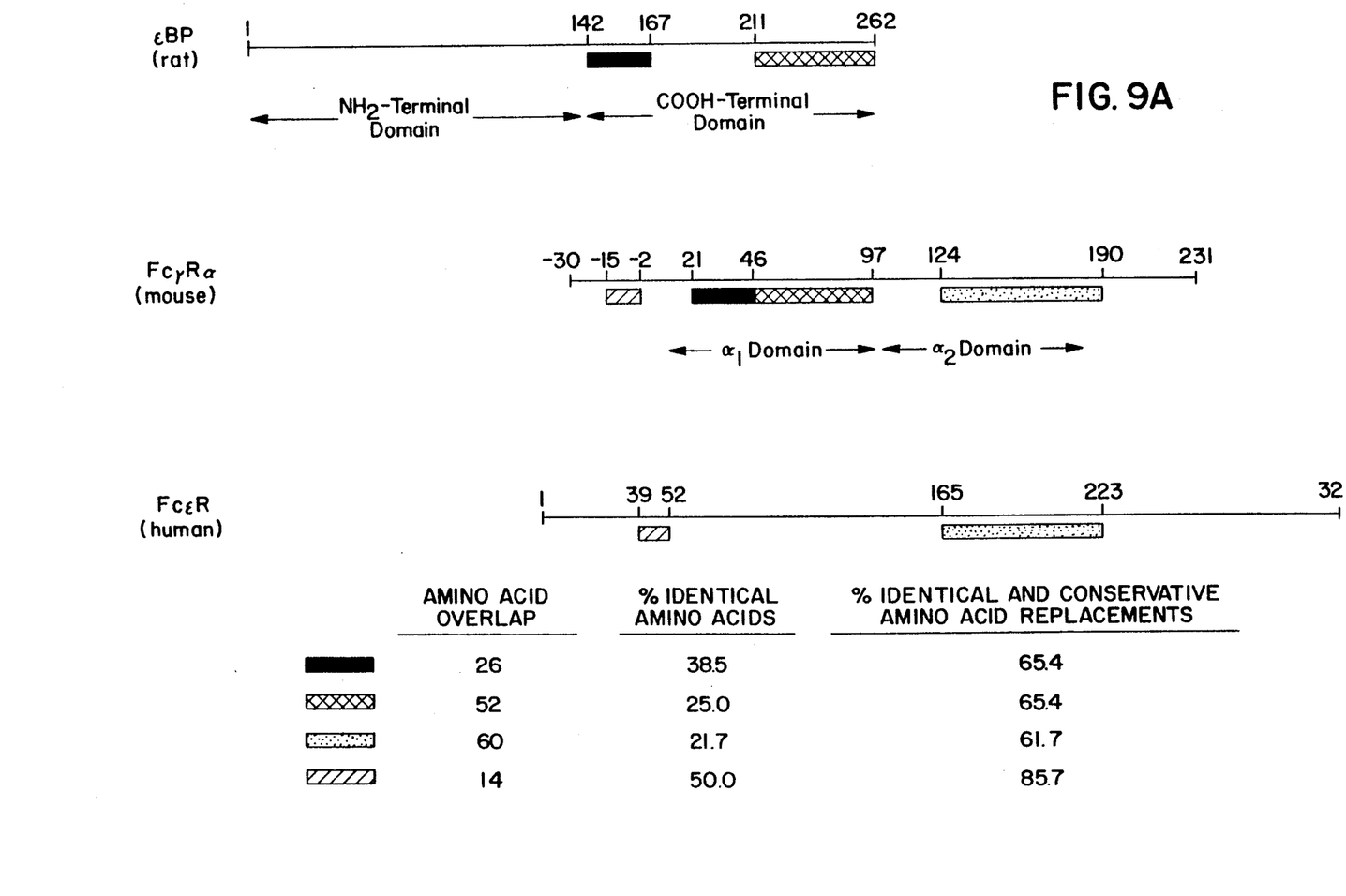
FIG. 9A demonstrates the amino acid sequence homology between εBP, FcγRα, and FcεR, displaying the sequences linearly with the amino terminus on the left and the carboxyl terminus on the right. The numbering scheme for εBP is as in FIG. 1. The numbering conventions for FcγRα and FcαR are as described. The program FASTP was used to identity regions of amino acid homology, which are indicated by boxes with various shadings.
Figure 9B:
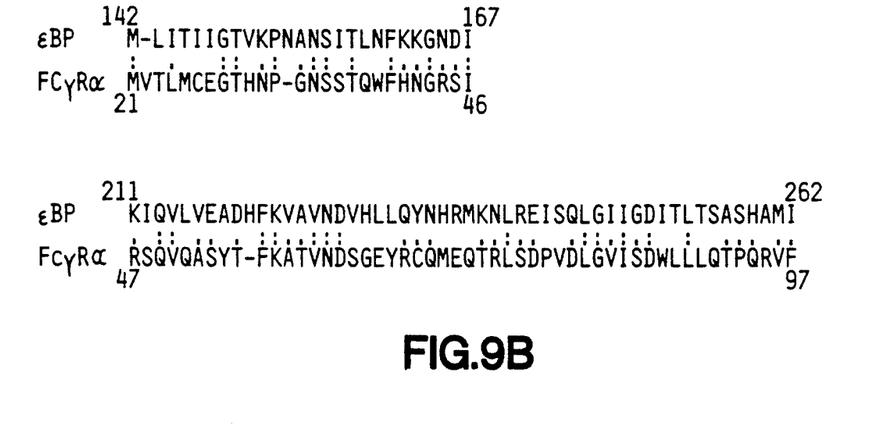
FIG. 9B compares the amino acid alignment of εBP and FcγRα (standard one-letter code). The FASTP program was again used; two dots indicate amino acid identity, and one dot indicates a conservative amino acid replacement. Gaps have been introduced to maximize the homology alignment.

We noted that a portion of human hymphocyte FcγR shares sequence homology with the $\alpha_2$ domain of mouse lymphocyte FcγR (FIG. 9A). Although the degree of homology is not high, it is probably significant, especially taking into consideration the sequence divergence that occurs between species. Since the mouse lymphocyte FcγR counterpart has not yet been identified in the IgE system, it would not be surprising to find additional FcεRs with a higher degree of homology to FcγRs, and it would be interesting to see if they share homology with εBP.

One characteristic shared by εBP and FcεR is their lack of a hydrophobic signal peptide at the amino terminus. In the case of FcεR, the location of a putative transmembrane segment near the amino terminus allows the prediction of its orientation with an intracellular amino terminus and an extracellular carboxyl terminus. However, εBP lacks an obvious membrane-spanning region. We do not know whether the amino-terminal repeated sequence, either by direct interaction with the membrane bilayer or by association with an integral membrane protein, allows εBP to function as a cell surface molecule.

Although εBP has very interesting structural features and an obvious relationship with FcγR, the function of this protein remains unknown. We have previously considered that εBP may be equivalent to either the β subunit of the high-affinity IgE receptor or the protein core of the highly glycosylated α subunit, as all these proteins have similar molecular weights (Metzger, H. et al, *Prog. Immunol. Proc. Int. Congr. Immunol.* 5, 493–501, 1983; Kulczycki, A., Jr. and Parker, C. W., *J. Biol. Chem.* 256, 10717–10723, 1981; Holowka, D. et al, *J. Receptor Res.* 1, 41–58, 1980; Kanellopoulos, J. M., Liu, T.-Y., Poy, G. and Metzger, H., *J. Biol. Chem.*, 255:9060–9066, 1980). However, comparison of the amino acid composition of εBP with the compositions reported for both the α (Kanellopoulos, J. M., Liu, T.-Y., Poy, G. and Metzger, H., *J. Biol. Chem.*, 255:9060-9066, 1980) and β (Metzger, H., Alearaz, G., Hohman, R., Kinet. J.-P., Pribluda, V. and Quarto, R., *Annu. Rev. Immunol.*, 4:419-470, 1986) subunits excludes this possibility. Furthermore, εBP lacks any potential N-linked carbohydrate attachment sites that would be required for the highly glycosylated α subunit.

It is possible that εBP represents another type of IgE receptor. Two distinct types of IgG receptors. $M_r$ 68,000 and 40,000, have been identified from a human monocyte line (Anderson, C. L., Guyre, P. M., Whitin, J. C., Ryan, D. H., Looney, R. J. and Fanger, M. W., *J. Biol. Chem.*, 261:12856-12864, 1986). Two receptors, activated by the same ligand and on the same cell, may trigger different pathways of cellular activation. Alternatively, εBP may be an intracellular protein necessary for recognition of internalized IgE. The role for an intracellular protein recognizing immunoglobulin is exemplified by an IgG-binding protein that is found in pre-B lymphocytes and that has a postulated function in the regulation of IgG heavy chains synthesis (Munro, S. and Pelham, H. R. B., *Cell, 46:291-300, 1986;* Haas, I. G. and Wahl, M., *Nature (London)*, 306:387-389, 1983).

The possibility also exists that εBP is a soluble secretory protein, similar to IgE-binding factors identified by others and shown to be secreted by restricted populations of lymphocytes (Ishizaka, K., *Annu. Rev. Immunol.*, 2:159-182, 1984). Although the lack of a signal peptide might argue against the secretion of εBP, interleukin 1 is one example of a secreted protein without a classical hydrophobic signal peptide common to most such proteins (Lomedico, P. T., Gubler, U., Hellmann, C. P., Dukovich, M., Giri, J. G., Pan, Y.-C. E., Collier, K. Semionow, R., Chua, A. O. and Mizel, S. B., *Nature (London)*, 312:458-462, 1984; Aaron, P. E., Webb, A. C., Rosenwaser, I. J., Mucci, S. F., Rich, A., Wolff, S. M. and Dinarello, C. A., *Proc. Natl. Acad. Sci. U.S.A.*, 81:7907-7911, 1984). Identification of the cellular location of εBP is clearly necessary to clarify all these possibilities.

Other proteins with similar two-domain structures have previously been described. Notably, the Cl4 component of complement and acetylcholinesterase both possess a globular domain attached to a collagen-like domain. The oligomeric form of Cl4 (Porter, R. R. and Reid, K. B. M., *Adv. Protein Chem.*, 33:1-71, 1979) is composed of interacting collagen-like domains forming a stalk capped by globular regions that bind the Fc portion of IgG. Since εBP binds selectively to the Fc portion of IgE, a similar functional arrangement could be considered. A multimeric arrangement has also been proposed for acetylcholinesterase in which the collagenous domain are postulated to interact with each other and anchor the enzyme to the basement membrane at the neuromuscular junction (Vigny, M., Martin, G. R. and Crotendorst, G. R., J. Biol. Chem., 258:8794-8798, 1983).

The functional roles played by IgE and IgE-binding molecules are diverse, ranging from the activation of mast cells and basophils to the regulation of IgE synthesis. Currently, the physiological role played by εBP with its unusual structure and IgE-binding property is unknown.

The invention may be embodied in any of several processes and compositions. One form in which the invention may be embodied and defined is an isolated IgE-binding protein εBP, consisting essentially of two domains, namely an amino-terminal domain comprising about 140 amino acids including the highly conserved repetitive amino acid sequence Tyr-Pro-Gly-Pro/Gln-Ala/Thr-Pro-Ala-Pro-Gly-Ala and a carboxyl-terminal domain comprising 122 amino acids which shares significant sequence homology with a domain of lymphocyte/macrophage receptor for the Fc portion of IgG. The term "isolated" as used here means that the composition, whatever and however defined, is isolated from or separated from or purified from, and therefor separate from other compositions with which it occurs in nature, i.e. the human immune system, or is produced by genetic engineering or other techniques such that the composition under consideration is separate from such other compositions with which it occurs in nature. A composition is said to consist essentially of the particular defined protein, DNA, etc. or other compound(s), when the defined compound(s) are separate from and not intermixed or reacted with other compounds which would substantially mask, diminish, confuse or alter the characteristics of the compound(s) under consideration in the setting and us for which the compound(s) is being considered. Compounds under consideration may, however, be mixed with carriers, adjuvents, non-interfering reagents, etc., and still be considered isolated and the composition regarded as consisting essentially thereof. With these definitions in mind, the invention may be embodied as isolated composition of matter consisting essentially of IgE-binding protein having substantially the amino acid sequence:

Met Ala Asp Gly Phe Ser Leu Asn Asp Ala Leu Ala Gly Ser
Gly Asn Pro Asn Pro Arg Gly Trp Pro Gly Ala Trp Gly Asn
Gln Pro Gly Ala Gly Gly Tyr Pro Gly Ala Ser Tyr Pro Gly
Ala Tyr Pro Gly Gln Ala Pro Pro Gly Gly Tyr Pro Gly Gln
Ala Pro Pro Ser Ala Tyr Pro Gly Pro Thr Gly Pro Ser Ala
Tyr Pro Gly Pro Thr Ala Pro Gly Ala Tyr Pro Gly Pro Thr
Ala Pro Gly Ala Pro Phe Pro Gly Gln Pro Gly Gly Pro Gly Ala
Tyr Pro Ser Ala Pro Gly Ala Tyr Pro Ser Ala Pro Gly Ala
Tyr Pro Ala Thr Gly Pro Phe Gly Ala Pro Thr Gly Pro Leu
Thr Val Pro Tyr Asp Met Pro Leu Pro Gly Gly Val Met Pro
Arg Met Leu Ile Thr Ile Ile Gly Thr Val Lys Pro Asn Ala
Asn Ser Ile The Leu Asn Phe Lys Lys Gly Asn Asp Ile Ala
Phe His Phe Asn Pro Arg Phe Asn Glu Asn Asn Arg Arg Val
Ile Val Cys Asn Thr Lys Gln Asp Asn Asn Trp Gly Arg
Glu Glu Arg Gln Ser Ala Phe Pro Phe Gly Ser Gly Lys
Pro Phe Lys Ile Gln Val Leu Val Glu Ala Asp His Phe
Lys Val Ala Val Asn Asp Val His Leu Leu Gln Tyr Asn
His Arg Met Lys Asn Leu Arg Glu Ile Ser Gln Leu Gly
Ile Ile Gly Asp Ile Thr Leu Thr Ser Ala Ser His Ala
Met Ile.

The invention may be embodied in the form of a composition of matter substantially isolated from other DNA consisting essentially of DNA encoding an IgE-binding protein having substantially the aforesaid amino acid sequence or in an IgE-binding protein prepared by isolating the genetic material coding for the IgE-binding polypeptide having substantially the specified amino acid sequences. In regard to the amino acid sequence, it will be understood that individual or a limited number of amino acids may be substituted as fragments of the overall protein sequence without changing its essential immunogenic and immunologice nature and such would be within the scope of the invention. Thus considered, the invention may be defined in terms of an IgE-binding protein harvested from host cells into which the cDNA encoding for the amino acid sequence. The IgE-binding protein has a molecular weight of approximately 31,000 daltons and at least five methionine residues. It is substantially devoid of potential N-glycosylation sites and is capable of reacting specifically with anti-εBP antiserum and binding the IgE-sepharose 4B.

INDUSTRIAL APPLICATIONS

Applicability has been discussed in the text of the preceding sections of this specification. Specifically, it has been discovered that: (1) a 31K IgE-binding protein can be translated in vitro from RBL mRNA and has been identified; (2) cDNA coding for this protein has been found to be novel; and (3) this protein has been shown to be expressed specifically in certain cell types known to possess IgE-specific receptors. Studies using the cDNA probe as well as antibodies against synthetic peptides corresponding to specific parts of the predicted sequence should further establish the expression of the described gene specifically in IgE-receptor positive cells, the localization of the protein in these cells and the role this protein may play in IgE-mediated activation of basophils and mast cells. Thus, the protein may be used as an IgE regulant or to absorb IgE, in effect an "IgE sponge", in the handling of allergenic reactions.

Modifications obvious to one with ordinary skill in the art may be made without departing from the scope of the present invention. For example, the genetic material used to form the cDNA may be induced by inserting other human cell lines containing the IgE-specific binding receptors or with other cell material other than RBL mRNA.

While the invention has been described in terms of rat IgE-binding protein, the methods are equally applicable to producing cDNAs useful in detecting related human equivalents or siderophones.

What is claimed is:

1. A composition of matter consisting essentially of DNA isolated from the cell components with which it occurs in nature, said DNA encoding an IgE-binding protein having substantially the amino acid sequence:

Met Ala Asp Gly Phe Ser Leu Asn Asp Ala Leu Ala Gly Ser
Gly Asn Pro Asn Pro Arg Gly Trp Pro Gly Ala Trp Gly Asn
Gln Pro Gly Ala Gly Gly Tyr Pro Gly Ala Ser Tyr Pro Gly
Ala Tyr Pro Gly Gln Ala Pro Pro Gly Gly Tyr Pro Gly Gln
Ala Pro Pro Ser Ala Tyr Pro Gly Pro Thr Gly Pro Ser Ala
Tyr Pro Gly Pro Thr Ala Pro Gly Ala Tyr Pro Gly Pro Thr
Ala Pro Gly Ala Phe Pro Gly Gln Pro Gly Gly Pro Gly Ala
Tyr Pro Ser Ala Pro Gly Ala Tyr Pro Ser Ala Pro Gly Ala
Tyr Pro Ala Thr Gly Pro Phe Gly Ala Pro Thr Gly Pro Leu
Thr Val Pro Tyr Asp Met Pro Leu Pro Gly Gly Val Met Pro
Arg Met Leu Ile Thr Ile Ile Gly Thr Val Lys Pro Asn Ala
Asn Ser Ile Thr Leu Asn Phe Lys Lys Gly Asn Asp Ile Ala
Phe His Phe Asn Pro Arg Phe Asn Glu Asn Asn Arg Arg Val
Ile Val Cys Asn Thr Lys Gln Asp Asn Asn Trp Gly Arg Glu
Glu Arg Gln Ser Ala Phe Pro Phe Glu Ser Gly Lys Pro Phe
Lys Ile Gln Val Leu Val Glu Ala Asp His Phe Lys Val Ala
Val Asn Asp Val His Leu Leu Gln Tyr Asn His Arg Met Lys
Asn Leu Arg Glu Ile Ser Gln Leu Gly Ile Ile Gly Asp Ile
Thr Leu Thr Ser Ala Ser His Ala Met Ile.

* * * * *